US011340276B2

(12) United States Patent
Foeger et al.

(10) Patent No.: US 11,340,276 B2
(45) Date of Patent: May 24, 2022

(54) TESTING DEVICE FOR CHECKING AT LEAST ONE FIRST MEDICAL ELECTRODE

(71) Applicant: Leonh. Lang, Innsbruck (AT)

(72) Inventors: Simon Foeger, Telfs (AT); Ronald Staerz, Sistrans (AT)

(73) Assignee: Leonh. Lang, Innsbruck (AT)

( * ) Notice: Subject to any disclaimer, the term of this patent is extended or adjusted under 35 U.S.C. 154(b) by 253 days.

(21) Appl. No.: 16/201,417

(22) Filed: Nov. 27, 2018

(65) Prior Publication Data

US 2019/0094281 A1    Mar. 28, 2019

Related U.S. Application Data

(63) Continuation of application No. PCT/AT2017/060138, filed on May 24, 2017.

(30) Foreign Application Priority Data

May 27, 2016   (AT) .............................. A 50479/2016

(51) Int. Cl.
*G01R 27/26* (2006.01)
*A61N 1/372* (2006.01)
(Continued)

(52) U.S. Cl.
CPC .......... *G01R 27/2605* (2013.01); *A61N 1/08* (2013.01); *A61N 1/3925* (2013.01); *G01R 31/58* (2020.01);
(Continued)

(58) Field of Classification Search
CPC .. G01R 27/2605; G01R 31/58; G01R 17/105; G01R 31/00; G01R 1/07; A61N 1/3925;
(Continued)

(56) References Cited

U.S. PATENT DOCUMENTS 4,200,104 A    4/1980 Harris
4,831,324 A *  5/1989 Asakura ................. G01R 27/22
                                                 204/404
(Continued)

FOREIGN PATENT DOCUMENTS

CA        2874744      12/2013
CN     102665539 A     9/2012
(Continued)

OTHER PUBLICATIONS

Agilent Impedance Measurement Handbook—A guide to measurement technology and techniques, 4th ed., 2009 (Year: 2009).*

*Primary Examiner* — Daniel R Miller

(57) ABSTRACT

The invention relates to a testing device for checking at least one first medical electrode (1), wherein the testing device comprises at least one first measuring electrode (2), which can be arranged relative to the first medical electrode (1) to be checked in such a way that the at least one first measuring electrode (2) and the first medical electrode (1) to be checked form a first capacitance ($C_{11}$); a signal generating device (3), by way of which an alternating current voltage can be generated, by means of which the first capacitance (Cn) can be acted upon; an evaluation device (4), which is designed to determine at least one first test result ($P_{11}$) in relation to the first capacitance ($C_{11}$) from a measured impedance curve (I) of an impedance caused in response to the first capacitance ($C_{11}$).

20 Claims, 6 Drawing Sheets

(51) Int. Cl.
*A61N 1/39* (2006.01)
*A61N 1/08* (2006.01)
*G01R 31/58* (2020.01)
*A61N 1/04* (2006.01)

(52) U.S. Cl.
CPC ....... *A61B 2560/0276* (2013.01); *A61N 1/046* (2013.01); *A61N 2001/37294* (2013.01)

(58) Field of Classification Search
CPC ............ A61N 1/08; A61N 2001/37294; A61N 1/046; A61N 1/36125; A61N 1/0492; A61N 1/04; A61N 2001/083; A61B 2560/0276; A61B 5/6833; A61B 5/04087; A61B 5/68335
See application file for complete search history.

(56) References Cited

U.S. PATENT DOCUMENTS

| | | | | |
|---|---|---|---|---|
| 6,028,433 | A * | 2/2000 | Cheiky-Zelina ... | G01N 33/2888 324/663 |
| 2003/0055478 | A1* | 3/2003 | Lyster ................. | A61N 1/0492 607/142 |
| 2005/0277991 | A1* | 12/2005 | Covey ................. | A61N 1/0492 607/5 |
| 2006/0022318 | A1* | 2/2006 | Koike ................. | A61N 1/0472 257/676 |
| 2007/0093871 | A1 | 4/2007 | Hoium et al. | |
| 2010/0056880 | A1* | 3/2010 | Cho .................... | A61B 5/02438 600/301 |
| 2012/0016210 | A1* | 1/2012 | Kim .................... | A61B 5/6838 600/301 |
| 2012/0019253 | A1* | 1/2012 | Ziegler ............... | G01R 31/392 324/433 |
| 2012/0179234 | A1 | 7/2012 | Carrington | |
| 2012/0299607 | A1 | 11/2012 | McIntyre et al. | |
| 2013/0320994 | A1 | 12/2013 | Brittain et al. | |
| 2015/0045869 | A1 | 2/2015 | Albright et al. | |

FOREIGN PATENT DOCUMENTS

| | | |
|---|---|---|
| DE | 2849422 A1 | 5/1979 |
| EP | 2527001 A1 | 11/2012 |
| WO | WO 2005115262 A1 | 12/2005 |
| WO | WO 2015143460 A1 | 10/2015 |

* cited by examiner

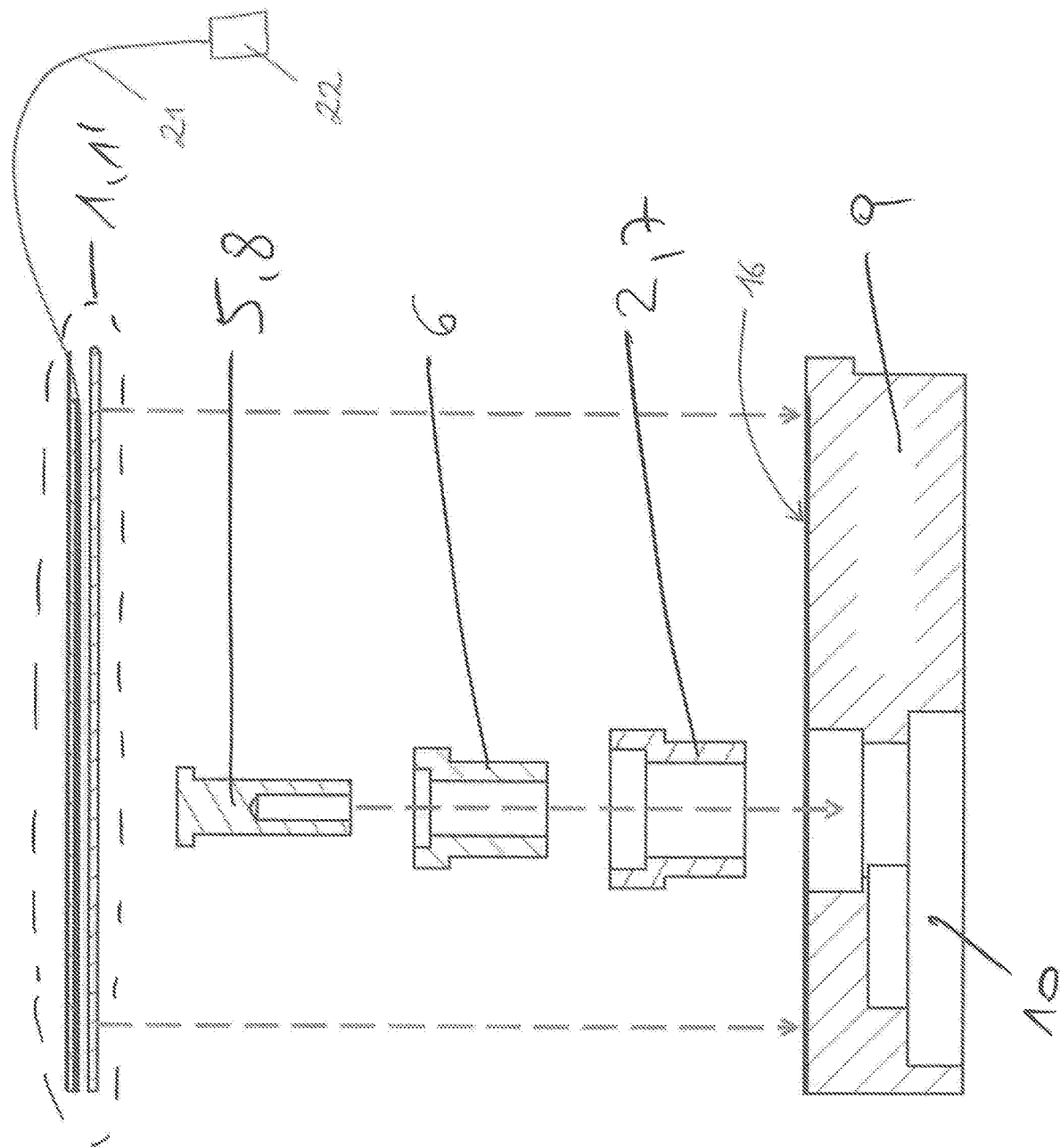

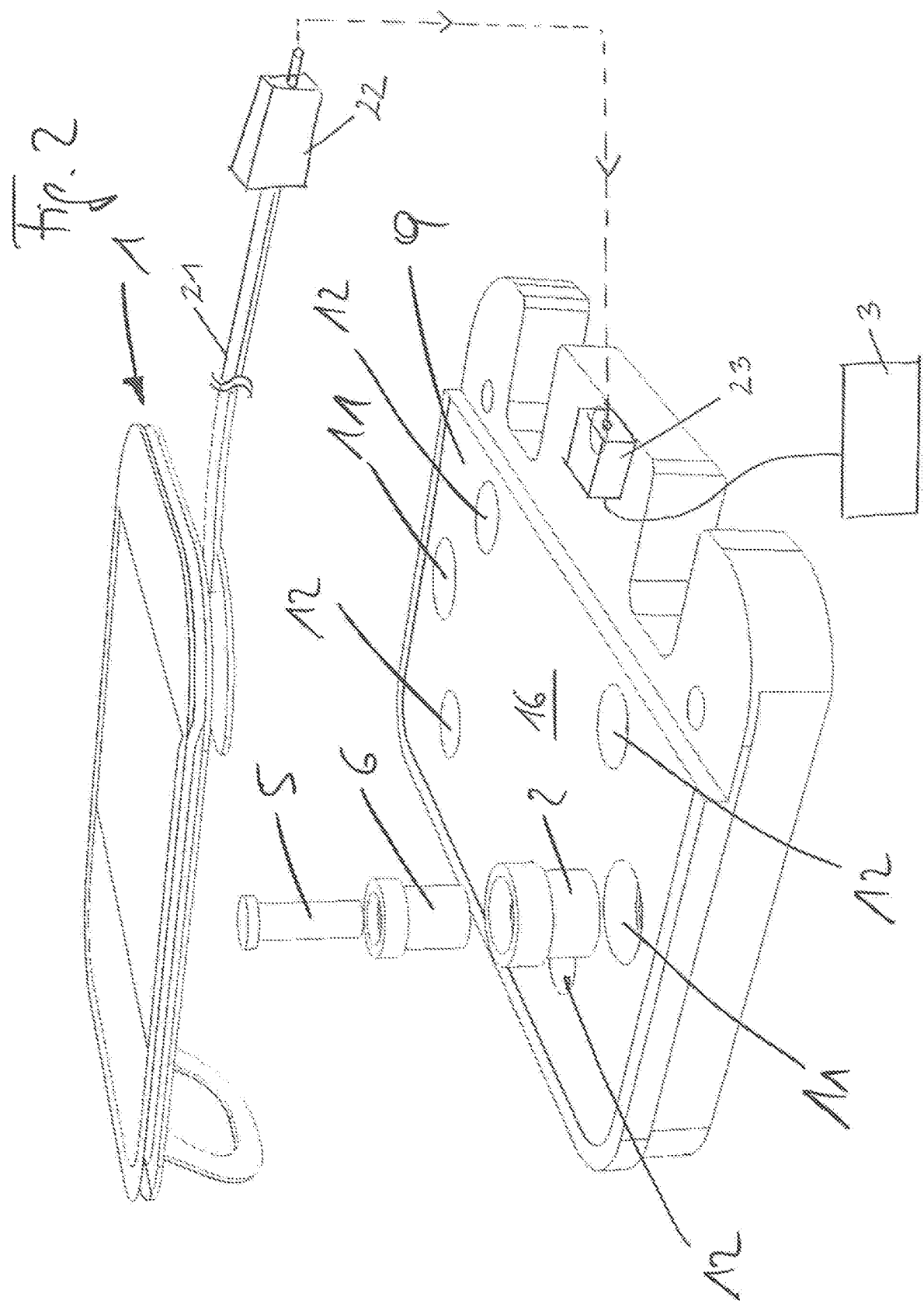

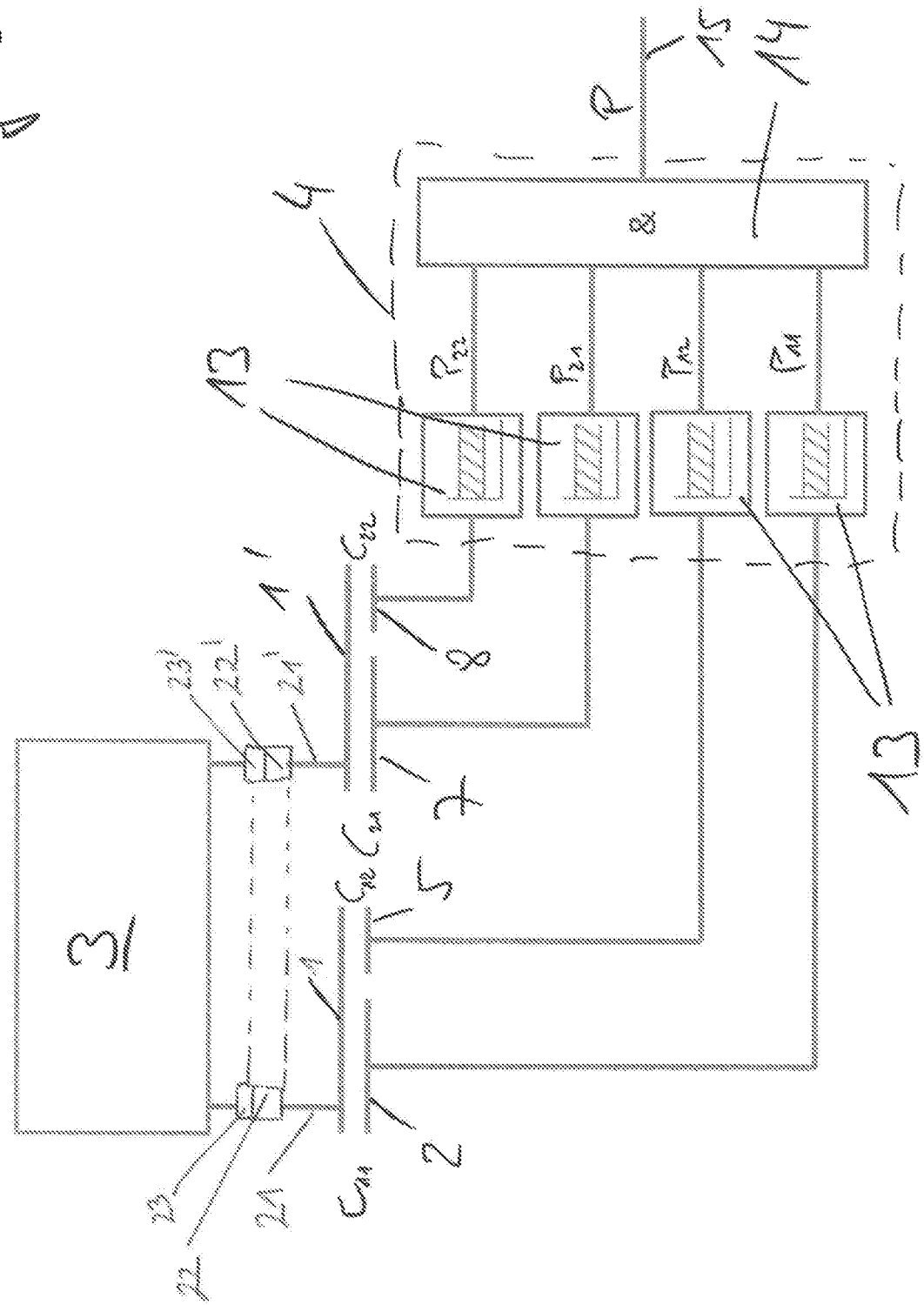

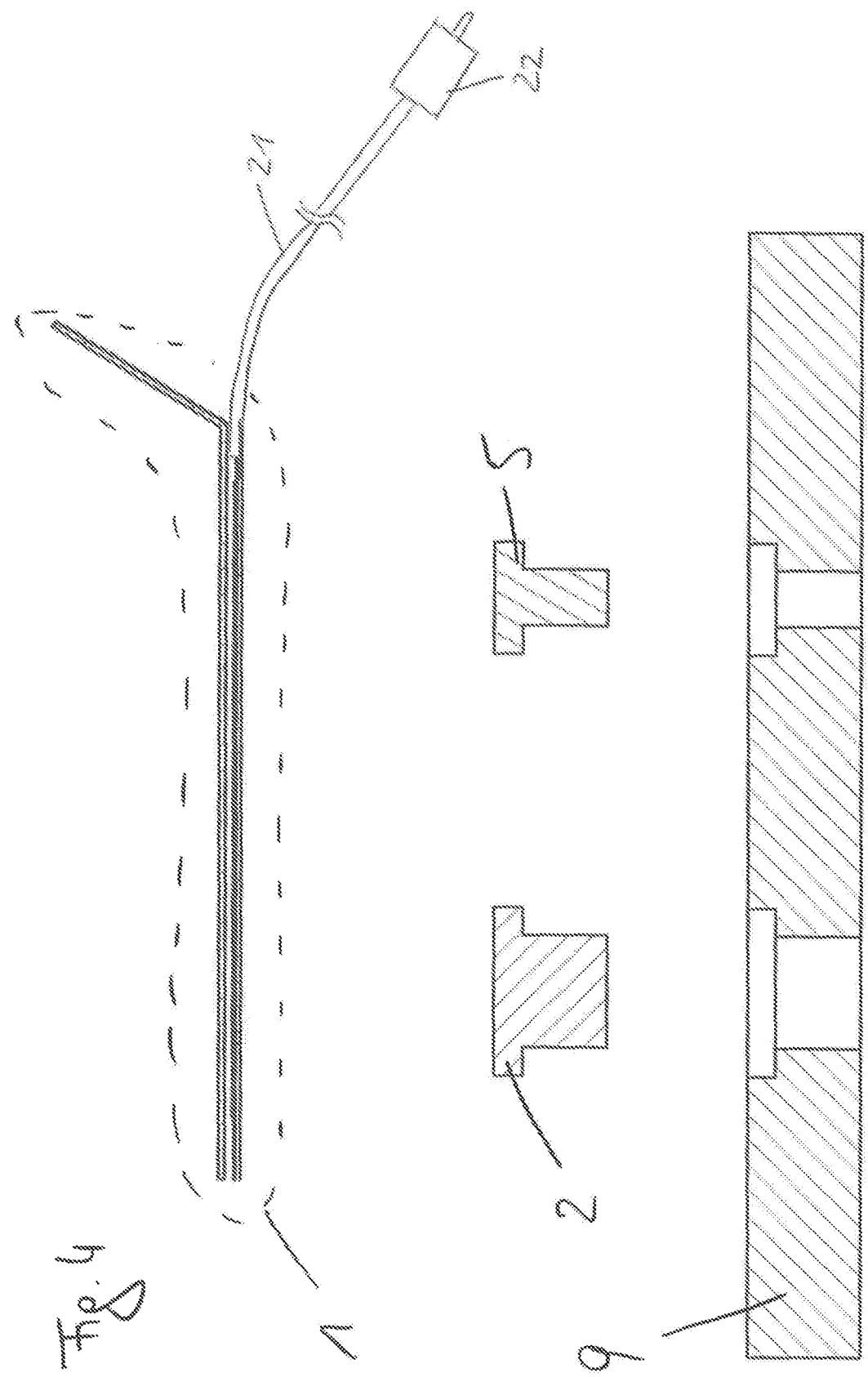

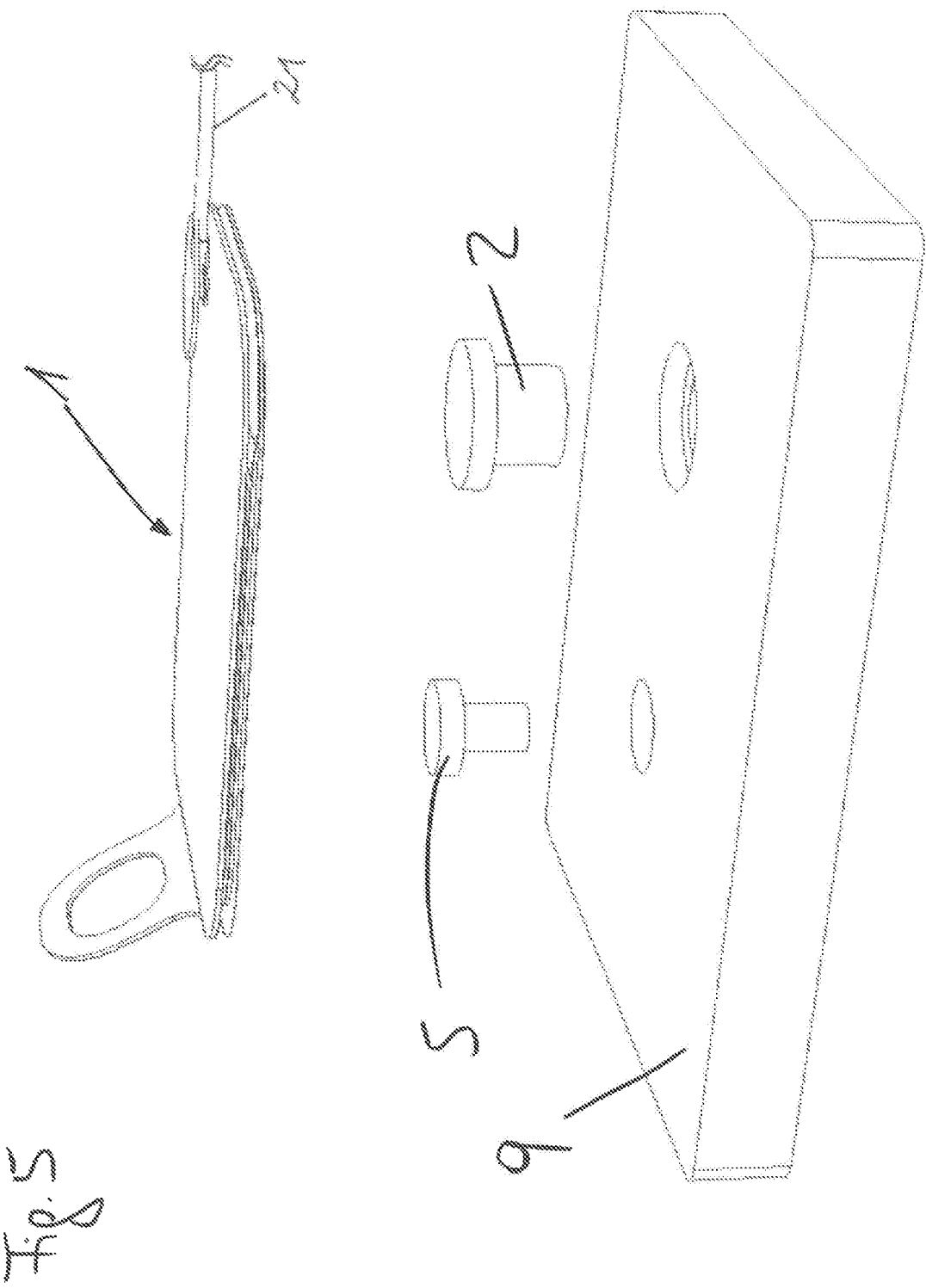

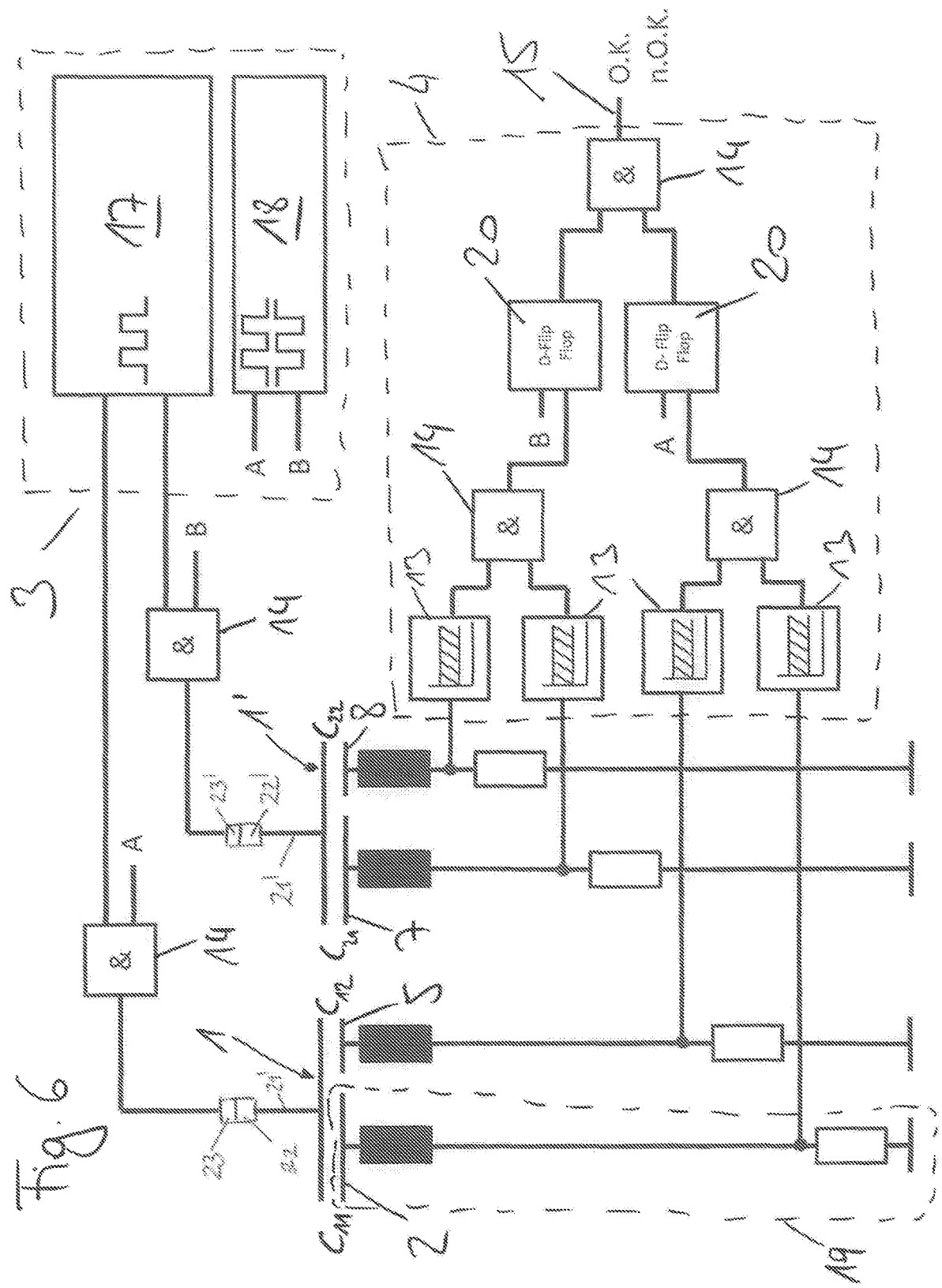

TESTING DEVICE FOR CHECKING AT LEAST ONE FIRST MEDICAL ELECTRODE

PRIORITY INFORMATION

The present application is a continuation of International Application No. PCT/AT2017/060138, filed May 24, 2017, which claims priority from Austrian Patent Application No. A 50479/2016, filed May 27, 2016, the contents of which are incorporated herein by reference in their entirety.

BACKGROUND OF THE INVENTION

1. Field of the Invention

The invention relates to a testing device for checking at least one medical electrode, having the features of the pre-characterising clause of claim 1.

2. Introduction

Electrodes to be checked emerge, for example, in US 2015/0045869 A1. This discloses two jointly assembled medical electrodes in the form of defibrillation electrodes.

Previous testing devices functioned on a purely manual basis, in that the presence of a contact between connections of the electrode and the actual electrode surface (conducting surface) was visually checked by an employee and the electrical connection was determined by means of a multimeter. The test step was to be provided separately to the value-adding processes. Such a procedure is error-prone and complex.

BRIEF DESCRIPTION OF THE DRAWINGS

An exemplary embodiment of the invention will be discussed with reference to the figures, in which:

FIG. 1 shows a section through the exploded view of FIG. 2.

FIG. 2 shows an exploded view of a first exemplary embodiment of a testing device according to the invention.

FIG. 3 shows a schematic representation of a testing device according to the invention.

FIG. 4 shows a section through the exploded view of FIG. 5.

FIG. 5 shows an exploded view of a second exemplary embodiment of a testing device according to the invention.

FIG. 6 shows a schematic circuit diagram of the testing device.

DETAILED DESCRIPTION

The object of the invention is to provide a testing device which allows at least partially automated testing, which can take place during a value-adding process.

This object is achieved by a testing device having the features of claim 1. Advantageous exemplary embodiments of the invention are defined in the dependent claims.

The testing device according to the invention operates without the production of a mechanical electrical contact between the medical electrode(s) to be checked and the measuring electrode(s). The testing process itself can be carried out fully automatically and the testing device can be fitted at least partially automatically.

A single (first) measuring electrode for carrying out the testing process is sufficient per se. In order to increase the safety (in particular safety against incorrect operation and manipulation safety and measurement stability of the test) the arrangement of at least one second measuring electrode can be provided. Only when the evaluation unit determines in relation to the signals of both resulting capacitances that the medical electrode has passed the test is the latter released. In such an embodiment, it is provided that the testing device further has at least one second measuring electrode, which can be arranged relative to the first medical electrode to be checked, in that the at least one second measuring electrode and the first medical electrode to be checked form a second capacitance, the evaluation device is designed to determine at least one second test result in relation to the second capacitance from a measured impedance curve of an impedance caused due to the second capacitance in response to an alternating voltage generated by the signal generating device.

In this case, it can preferably be provided that the surfaces of the at least one first and the at least one second measuring electrode are different sizes. This allows two different release windows to be used in relation to the one medical electrode to be tested, even when only one alternating voltage is used with one frequency.

The first and the second measuring electrodes can be arranged arbitrarily per se in relation to the electrode to be checked (for example side by side).

However, in order to achieve a compact arrangement it is preferably provided that the at least one first measuring electrode is in the form of a circular ring and the at least one second measuring electrode is arranged within the circular ring and is electrically isolated from the circular ring by an insulator.

It is preferably provided that the testing device is designed for joint or simultaneous checking of at least one first medical electrode and a second medical electrode. For example, defibrillation electrodes have a pair of electrodes, and other medical electrodes can be combined in a smaller (in other words, in isolation) or in a larger number to form a functional unit. In this embodiment, the testing device further has:

at least one third measuring electrode, which can be arranged relative to the second medical electrode to be checked such that the at least one third measuring electrode and the second medical electrode to be checked form a third capacitance, wherein the signal generating device is designed to generate an alternating voltage by means of which the third capacitance can be acted upon the evaluation device, which is designed to determine at least one first test result in relation to the third capacitance from a measured impedance curve of an impedance caused due to the third capacitance in response to the alternating voltage generated by the signal generating device.

Naturally, joint or simultaneous checking can be carried out in such a way that the signal generating device successively acts upon the individual capacitances with the alternating voltage and/or that the evaluation device successively measures the impedance curves in relation to the individual capacitances. However, no mechanical manipulation of the medical electrodes to be checked is required in the event of joint or simultaneous checking.

It is preferably provided that the application of the alternating voltage to at least one of the existing capacitances can be generated in such a way that the signal generating device acts upon the first and/or the second medical electrode(s) to be checked.

The testing device itself can preferably be designed in such a way that the testing device has at least one receiving region, preferably in the form of a planar supporting surface, which is designed to receive at least one, preferably a plurality of, medical electrode(s) to be checked, wherein the measuring electrode(s) is/are arranged in the receiving region. The electrode to be checked or the electrode pair to be checked can thereby simply be placed on the receiving region, whereupon the capacitive measurement is then carried out.

To connect the electrodes to the signal generating device it can advantageously be provided that at least one electrical connecting element, which is preferably connected to the signal generating device, is preferably arranged in the region of a receiving region for at least one electrode to be checked, to which element at least one connector plug of a connecting cable leading to the medical electrode can be detachably connected.

With a design of this kind the connector plug of the connecting cable of the electrode to be checked is simply inserted into the fixed connecting element and is thereby electrically connected to the signal generating device.

Overall, the testing device according to the invention can be used to check not only the medical electrode itself, but also the connecting cable or conducting connection thereof.

In the case of two or more electrodes, the correctness (polarity) of the connecting cables can also be checked in any connector plugs. This is particularly advantageous when, in the case of two electrodes, two connecting cables lead to a double connector plug which has mechanical means in order to be used, for example, only in the correct position, in other words in the correct polarity, in an ECG device. If the connecting cables of the two electrodes were interchanged, the polarity would be wrong and the testing device according to the invention would detect this fault. This wrongly connected double electrode is then rejected and is not attached to the skin of a patient, in particular a human one.

One aspect of the invention consists in the use of a testing device, which is separate from the skin of the patient, for checking at least one medical electrode before it is applied, in particular adhesively bonded, to the skin of the patient.

There are already capacitive testing devices which test the transition impedance of a medical electrode to the skin of the patient in the adhesively bonded state of the electrode. However, this is not a testing device for the electrodes themselves, but a testing device for correct adhesion to the skin. According to the inventive use, electrodes or pairs of electrodes that are defective or incorrect in polarity are not used at all and can already be segregated beforehand.

As already mentioned, the testing device according to the invention not only checks the electrode itself in a preferred use, but also the connecting cable thereof or optionally present connector plugs. The totality of the electrode, connecting cable, connector plug, as sold as a unit, in particular in a package, is therefore capacitively checked even before being attached to the skin of the patient.

The reference numerals $C_{11}$, $C_{12}$, $C_{21}$, $C_{22}$ are used below for the first to fourth capacitance, which can be present between different medical electrodes to be checked and different measuring electrodes. The use of different short designations naturally does not mean that the numerical values of the different capacitances cannot be the same.

The first exemplary embodiment of a testing device according to the invention, which is shown in FIGS. 1 and 2, is suitable for joint testing of two medical electrodes (a first and a second medical electrode 1, 1') and, more precisely, in each case with two measuring electrodes (in relation to the first medical electrode 1 to be checked, these are the first measuring electrode and the second measuring electrode 2, 5 and in relation to the second medical electrode 1' to be checked these are the third and fourth measuring electrodes 7, 8). The four capacitances $C_{11}$, $C_{12}$, $C_{21}$, $C_{22}$ are present during the test.

The testing device has a receiving region 16, which is designed here for simultaneously receiving two medical electrodes 1, 1' to be tested. The medical electrodes 1, 1' to be tested should be arranged in the receiving region 16 in such a way that their actual electrode surfaces (conducting surfaces) point away from the receiving region 16. The back sides of the medical electrodes 1 to be checked 1, 1' are fixed for testing by way of vacuum (the openings 12 are used for applying the same). Therefore, there is no direct electrical contact between the conducting surfaces of the medical electrodes 1, 1' to be checked and the measuring electrodes 2, 5, 7, 8. If there is a desire to arrange the medical electrodes 1, 1' to be tested with their front sides in the receiving region 16, separate insulators would have to be arranged between the conducting surfaces and the measuring electrodes.

The second exemplary embodiment of a testing device according to the invention, which is shown in FIGS. 4 and 5, is suitable for testing a medical electrode 1 and has two measuring electrodes 2, 5. These are arranged side by side, but could also be designed in the same way as in the exemplary embodiment in FIGS. 1 and 2. The two capacitances $C_{11}$, $C_{12}$ are present during the test. The support 9 can therefore be designed as in the exemplary embodiment of FIGS. 1 and 2.

The connecting cable 21 for the medical electrode 1, at the free end of which a connector plug 22 is provided, can be seen in the exemplary embodiment illustrated in FIG. 2. The connector plug is merely schematically illustrated.

A connecting element 23 is arranged next to the receiving region 16 for the medical electrode to be checked, into which element the connector plug 22 can be inserted for checking. The signal generating device can then act upon the medical electrode, in particular with an alternating voltage, via the connecting element 23, the inserted connector plug 22 and the connecting cable 21.

The connecting cable and the connector plug 22, in addition to the electrode 1 itself, are checked for functional capability, in particular electrical conductivity, by means of this testing device.

FIG. 3 shows very schematically the construction of a testing device in accordance with the invention according to the first exemplary embodiment, having:

a first and a second measuring electrode 2, 5, which can be arranged relative to the first medical electrode 1 to be checked such that the first measuring electrode 2 and the first medical electrode 1 to be checked form a first capacitance $C_{11}$ and the second measuring electrode 5 and the first medical electrode 1 to be checked form a second capacitance $C_{12}$.

a third and a fourth measuring electrode 7, 8, which can be arranged relative to the second medical electrode 1' to be checked such that the third measuring electrode 7 and the second medical electrode 1' to be checked form a third capacitance $C_{21}$ and the fourth measuring electrode 8 and the second medical electrode 1' to be checked form a fourth capacitance $C_{22}$.

a signal generating device 3, by way of which an alternating voltage can be generated, by means of which the first to fourth capacitance $C_{11}$, $C_{12}$, $C_{21}$, $C_{22}$ can be acted upon.

an evaluation device 4, which is designed to determine a first to fourth test result $P_{11}$, $P_{12}$, $P_{21}$, $P_{22}$ in relation to the first to fourth capacitance $C_{11}$, $C_{12}$, $C_{21}$, $C_{22}$ and to determine an overall test result P in relation to the first to fourth capacitance $C_{11}$, $C_{12}$, $C_{21}$, $C_{22}$ from a measured impedance curve I of an impedance caused in response to the first to fourth capacitance $C_{11}$, $C_{12}$, $C_{21}$, $C_{22}$.

In the exemplary embodiment illustrated in FIG. 3 the connecting cables 21, 21' and their connector plugs 22, 22' can likewise be checked, wherein the connector plugs 22, 22' can be inserted into connecting elements 23, 23'.

As indicated by dashed lines, the connector plugs 22, 22' can be connected to a double connector plug which has two electrical connections. The same applies to the connection elements 23, 23'. These can likewise be connected to a double connection element.

Mechanical aligning means which are known per se can then preferably be provided and these ensure that the double connector plug 22, 22' is not inserted into the double connection element 23, 23' in an inverted manner. Aligning means of this kind are known to the person skilled in the art, for example, connecting pins of different sizes or asymmetrical projections or grooves on the plug can be used in order to avoid an inverted insertion. Once the double connector plug 22, 22' has been inserted into the double connection element 23, 23' in the correct position, the testing device according to the invention can then determine whether the connecting cable from the connector plug really leads to the electrode 1 and not (incorrectly) to the electrode 1'. In this way the correctness of the polarity of the double electrode 1, 1' can be checked irrespective of the conductivity of the connecting cables and the correct electrode structure per se.

FIG. 6 shows a detailed representation of FIG. 3. It can be seen that the signal generating device 3 comprises a frequency generator 17 and a clock 18. The frequency generator 17 acts upon the two medical electrodes 1, 1' to be checked with an alternating voltage. The clock 18 has an output A and an output B. The output A is associated with the first medical electrode 1 to be checked and is linked via an AND element 14 to an output of the frequency generator 17 associated with the first medical electrode 1 to be checked. The output B is associated with the second medical electrode 1' to be checked and is linked via an AND element 14 to an output of the frequency generator 17 associated with the second medical electrode 1' to be checked. This ensures that the two medical electrodes 1, 1' to be checked are not acted upon simultaneously by the alternating voltage.

The outputs A, B of the clock 18 are furthermore each linked to a flip-flop 20 of the evaluation device 4. It is therefore possible to assign from which of the two medical electrodes 1, 1' to be checked test signals are arriving.

Each of the four capacitances $C_{11}$, $C_{12}$, $C_{21}$, $C_{22}$ is part of a resonant circuit 19 with an inductance and an electrical resistance (for the sake of clarity, only one of the resonant circuits is provided with the reference numeral 19).

The impedance curve I resulting from the applied alternating voltage in each resonant circuit 19 is supplied to an analysis device 13 of the evaluation device 4 which checks whether the impedance curve I is in a predetermined window. If this is the case, the respective analysis device 13 outputs a positive test result $P_{11}$, $P_{12}$, $P_{21}$, $P_{22}$. A test result is formed for each of the medical electrodes 1, 1' to be checked via an AND element 14. An overall test result P for both medical electrodes 1, 1' to be checked is formed via a further AND element 14 and output via the output 15.

The testing device according to the invention is particularly suitable for use as a testing device separate from the skin of the patient for checking at least one medical electrode before its application to the skin of the patient. Medical electrodes that are found to be faulty can then already be rejected in advance and are not used at all on the patient. With the testing device according to the invention it is possible to check not only the electrode itself but also its connecting cable and its connector plug, in particular also in the case of a double electrode having a double connector plug, since the correctness of the polarity can be checked.

The medical electrode, including the connecting cables and connector plugs, can be checked before packaging thereof into a packaging sleeve, so rejected electrodes are not packaged from the outset. However, it is also conceivable to check the electrodes within a (part) packaging since the capacitive test can in principle take place through the packaging sleeve.

LIST OF REFERENCE NUMERALS 1 first medical electrode to be checked
1' second medical electrode to be checked
2 first measuring electrode
3 signal generating device
4 evaluation device
5 second measuring electrode
6 insulator
7 third measuring electrode
8 fourth measuring electrode
9 support
10 space for electrically contacting the measuring electrodes
11 receiving opening for measuring electrodes
12 openings for applying a vacuum
13 analysis device
14 AND element
15 output
16 medical electrode(s) receiving region
17 frequency generator
18 clock
19 resonant circuit
20 flip-flop
21, 21' connecting cable
22, 22' connector plug
23, 23' connection element
$C_{11}$ first capacitance (between a first medical electrode to be checked and a first measuring electrode).
$C_{12}$ second capacitance (between a first medical electrode to be checked and a second measuring electrode).
$C_{21}$ third capacitance (between a second medical electrode to be checked and a third measuring electrode.
$C_{22}$ fourth capacitance (between a second medical electrode to be checked and a fourth measuring electrode).
I impedance curve
$P_{11}$ first test result (in relation to a first electrode to be checked and a first measuring electrode).
$P_{12}$ second test result (in relation to a first electrode to be checked and a second measuring electrode).
$P_{21}$ first test result (in relation to a second electrode to be checked and a first measuring electrode).
$P_{22}$ second test result (in relation to a second electrode to be checked and a second measuring electrode).
P overall test result.

We claim:
1. Testing device for checking at least one first medical electrode (1), characterised in that the testing device has:

at least one first measuring electrode (2), which can be arranged relative to the first medical electrode (1) to be checked, in that the at least one first measuring electrode (2) and the first medical electrode (1) to be checked form a first capacitance (C11);

a signal generating device (3), by way of which an alternating voltage can be generated, by means of which the first capacitance (C11) can be acted upon; and an evaluation device (4), which is designed to determine at least one first test result (P11) in relation to the first capacitance (C11) from a measured impedance curve (I) of an impedance caused in response to the first capacitance (C11) being acted upon by the alternating voltage, wherein:

the testing device further comprises at least one second measuring electrode (5), which can be arranged relative to the first medical electrode (1) to be checked, in that the at least one second measuring electrode (5) and the first medical electrode (1) to be checked form a second capacitance (C12); and the evaluation device (4) is designed to determine at least one second test result (P12) in relation to the second capacitance (C12) from a measured impedance curve (I) of an impedance caused due to the second capacitance (C12) in response to an alternating voltage generated by the signal generating device (3).

2. Testing device according to claim 1, wherein:

the testing device further comprises a plurality of second measuring electrodes (5), which can be arranged relative to the first medical electrode (1) to be checked, in that the plurality of second measuring electrodes (5) and the first medical electrode (1) to be checked form a second capacitance (C12); and the evaluation device (4) is designed to determine a plurality of second test results (P12) in relation to the second capacitance (C12) from a measured impedance curve (I) of an impedance caused due to the second capacitance (C12) in response to an alternating voltage generated by the signal generating device (3).

3. Testing device according to claim 1, wherein the surfaces of the at least one first and the at least one second measuring electrode (2, 5) are different sizes.

4. Testing device according to the preceding claim, wherein the at least one first measuring electrode (2) is designed as a circular ring and the at least one second measuring electrode (5) is arranged within the circular ring and is electrically isolated from the circular ring by an insulator (6).

5. The testing device according to claim 1, wherein the testing device is designed to jointly check at least one first medical electrode (1) and a second medical electrode (1'), and further has:

at least one third measuring electrode (7), which can be arranged relative to the second medical electrode (1') to be checked, in that the at least one third measuring electrode (7) and the second medical electrode (1') to be checked form a third capacitance (C21), wherein the signal generating device (3) is designed to generate an alternating voltage, by means of which the third capacitance (C21) can be acted upon; and the evaluation device (4), which is designed to determine at least one first test result (P21) in relation to the third capacitance (C21) from a measured impedance curve (I) of an impedance caused due to the third capacitance (C21) in response to the alternating voltage generated by the signal generating device (3).

6. Testing device according to claim 5, wherein:

the testing device further has at least one fourth measuring electrode (8), which can be arranged relative to the second medical electrode to be checked (1'), in that the at least one fourth measuring electrode (8) and the second medical electrode (1') to be checked form a fourth capacitance (C22); and the evaluation device (4) is designed to determine at least one second test result (P22) in relation to the fourth capacitance (C22) from a measured impedance curve (I) of an impedance caused due to the fourth capacitance (C22) in response to an alternating voltage generated by the signal generating device (3).

7. Testing device according to claim 6, wherein the surfaces of the at least one third and the at least one fourth measuring electrode (7, 8) are different sizes.

8. Testing device according to claim 7, wherein the at least one third measuring electrode (7) is designed as a circular ring and the at least one fourth measuring electrode (8) is arranged within the circular ring and is electrically isolated from the circular ring by an insulator (6).

9. The testing device of claim 5, wherein an application of the alternating voltage to at least one of the capacitances (C11, C12, C21, C22) can be generated in such a way that the signal generating device (3) acts upon the first and/or the second medical electrode to be checked (1, 1').

10. Testing device according to claim 9, wherein the evaluation device (4) is connected to the first and/or the second and/or the third and/or the fourth measuring electrode (2, 5, 7, 8).

11. The testing device according to any one of claims 1-10, wherein the evaluation device (4) has at least one analysis device (13) which checks whether the measured impedance profile (I) of an associated capacitance (C11, C12, C21, C22) lies within a predetermined test window and, if this is the case, emits a positive test result (P11, P12, P21, P22) corresponding to the respective capacitance (C11, C12, C21, C22).

12. Testing device according to claim 11, wherein the evaluation device (4) has an AND element (14) which emits a positive overall test result (P) for a measured electrode (1, 1') or a totality of all measured electrodes (1, 1') only when a positive test result (P11, P12, P21, P22) exists for all measured capacitances (C11, C12, C21, C22).

13. Testing device according to claim 11, wherein the testing device has a receiving region (16), preferably in the form of a planar support surface, designed to receive at least one, preferably a plurality of, medical electrode(s) (1, 1') to be checked, wherein the measuring electrode(s) (2, 5, 7, 8) is/are arranged in the receiving region (16).

14. Testing device according to claim 13, wherein at least one opening (12) is arranged in the receiving region (16) in order to apply a vacuum to the medical electrode(s) (1, 1') to be checked.

15. The testing device according to any one of claims 1-10, wherein arranged preferably in a region of a receiving region (16) for at least one electrode to be checked is at least one electrical connection element (23), preferably connected to the signal generating device (3), to which element at least one connector plug of a connecting cable (21, 21') leading to the medical electrode can be detachably connected.

16. The testing device according to any one of claims 1-10, wherein the measuring electrode (2, 5, 7, 8) on the one hand and the medical electrodes to be brought into contact with a skin of a patient on the other hand are different electrodes.

17. A method for use with a testing device, which is separate from a skin of a patient, for checking at least one medical electrode (1, 1') before it is applied to the skin of the patient, the method comprising:
- causing a first capacitance (C11) to be formed using a first measuring electrode (2) and a medical electrode (1);
- causing a second capacitance (C12) to be formed using a second measuring electrode (5) and the medical electrode (1);
- generating an alternating voltage via a signal generating device (3);
- causing a first impedance in response to the first capacitance (C11) being acted upon by the alternating voltage;
- causing a second impedance in response to the second capacitance (C12) being acted upon by the alternating voltage;
- determining, via an evaluation device (4), a first test result (P11) in relation to the capacitance (C11) from a measured impedance curve (I) based on the impedance, to yield a first determination;
- determining, via the evaluation device (4), a second test result (P12) in relation to the capacitance (C11) from the measured impedance curve (I) based on the impedance, to yield a second determination;
- thereafter, based on the first determination and the second determination, applying the at least one medical electrode (1, 1') to the skin of the patient.

18. The method of claim 17, the method further comprising:
- applying the alternating voltage from the signal generating device (3) to the at least one medical electrode (1, 1') via a connecting cable(s) (21, 21') or a connector plug(s) (22, 22').

19. The method of claim 17 or claim 18, wherein the at least one medical electrode is located in a closed package.

20. A testing device comprising:
- a first measuring electrode;
- a second measuring electrode;
- a medical electrode, wherein the first measuring electrode and the medical electrode form a first capacitor;
- a signal generating device the generates first alternating voltage to apply to the first capacitor; and
- an evaluation device that determines a test result based on measuring an impedance curve of the first capacitor when the first alternating voltage is applied to the first capacitor, wherein:
  - the second measuring electrode is arranged relative to the medical electrode to be checked such that the second measuring electrode and the medical electrode to be checked form a second capacitor; and
  - the evaluation device is designed to determine a second test result in relation to the second capacitor from a measured impedance curve of an impedance caused due to the second capacitor in response to a second alternating voltage generated by the signal generating device.

* * * * *